Figure 3:
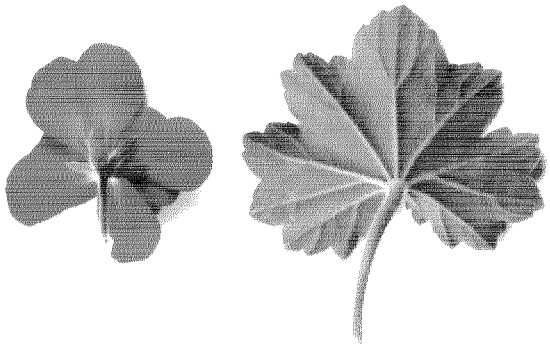

US00PP10813P

United States Patent [19]

Guillou

[11] Patent Number: Plant 10,813

[45] Date of Patent: Mar. 2, 1999

[54] GERANIUM PLANT NAMED GUISOL

[75] Inventor: Bernard Guillou, Saint-Malo, France

[73] Assignee: ETS. Guillou Freres, Saint-Malo, France

[21] Appl. No.: 592,182

[22] Filed: Jan. 26, 1996

[51] Int. Cl.[6] ..... A01H 5/00

[52] U.S. Cl. ..... Plt./87.12

[58] Field of Search ..... Plt./87.12

[56] References Cited

PUBLICATIONS

GTITM UPOVROM citation for FR PBR 150936 for *Pelargonium* 'Guisol', published May 10, 1993.

GTITM UPOVROM citation for NL PBR GRM02H9 for *Pelargonium* 'Guisol' published Jul. 16, 1993.

GTITM UPOVROM citation for DE PBR PEL 00872 for *Pelargonium* 'Guisol' published Aug. 15, 1993.

*Primary Examiner*—James R. Feyrer

*Attorney, Agent, or Firm*—Foley & Lardner

[57] ABSTRACT

A New and distinct cultivar of geranium plant named 'Guisol' characterized by its dark-red and double-type flowers; good branching and medium-green foliage with weak to absent zonation.

1 Drawing Sheet

The present invention comprises a new and distinct cultivar of geranium, botanically known as *Pelargonium zonale, × Pelargonium peltatum* and hereinafter referred to by the cultivar name 'Guisol'.

'Guisol' is a product of planned breeding program which had the objective of creating new geranium cultivars with double intermediate dark-red flowers with a plant habit that is between a zonal and an ivy geranium.

'Guisol' was originated from a hybridization made in a controlled breeding program in Saint-Malo, Bretagne, France. The female and male parents were unnamed hybrids from the proprietary Guillou collection, both parents being characterized by red double flowers.

'Guisol' was discovered and selected as one flowering plant within the progeny of the stated cross by the inventors in 1991 in a controlled environment in Saint-Malo, Bretagne, France.

The first act of asexual reproduction of 'Guisol' was accomplished when vegetative cuttings were taken from the initial selection in 1993 in a ,controlled environment in Saint Malo, Bretagne, France by a technician working under the supervision of the inventor. Horticultural examination of selected units initiated in 1994 in Hannover, Germany has demonstrated that the combination of characteristics as herein disclosed for 'Guisol' are firmly fixed and are retained through successive generations of asexual reproduction.

'Guisol' has not been observed under all possible environmental conditions. The phenotype may vary with variations in environment such as temperature, light intensity, and day length, without a change in genotype. The following observations, measurements and comparisons describe plants grown in Hannover, Germany under greenhouse conditions which approximate those generally used in commercial practice.

The following traits have been repeatedly observed and are determined to be basic characteristics of 'Guisol' which in combination distinguish this geranium as a new and distinct cultivar:

1. A geranium with characteristics exhibited by both a zonal and an ivy geranium.
2. Dark-red double-type flowers
3. Good branching plant habit.
4. Medium-green foliage with absent to very weak zonation.

Of the many commercial cultivars known to the present inventors there is no cultivar which can be closely compared to 'Guisol'.

Figure 2:
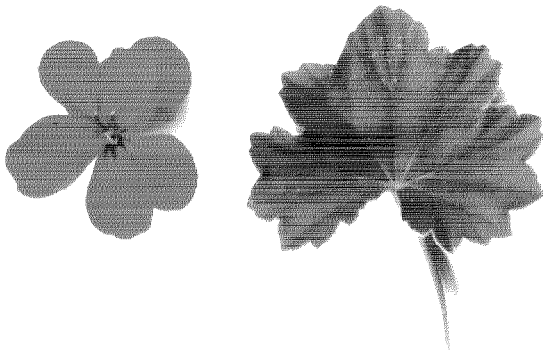
Figure 1:
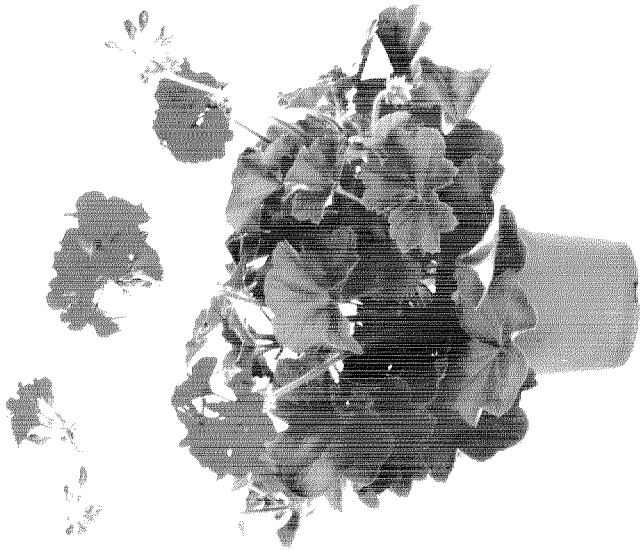

The accompanying photographic drawing show typical flower and foliage characteristics of 'Guisol'. FIG. 1 is a side view of 'Guisol'. FIG. 2 is a view of the upper side of a typical leaf and flower of the cultivar. FIG. 3 is a view of the under side of a typical leaf and flower of 'Guisol'.

In the following description color references are made to The Royal Horticultural Society (R.H.S.) Colour Chart. The color values were determined in 1994 under greenhouse conditions at Hannover, Germany.

Classification:

*Botanical.*—*Pelargonium zonale* × *Pelargonium peltatum.*

*Commercial.*—Ivy geranium cultivar 'Guisol'.

Inflorescence

Umbel:

*Average diameter.*—50–60 mm.

*Average depth.*—40–50 mm.

*Peduncle length.*—170 mm.

*Pedicel length.*—10 mm.

*Flowers.*—12 to 25 flowers per umbel; the number of flowers per umbel varies with age and plant vigor.

Corolla:

*Form.*—Double-type with many petals.

*Color (general tonality from a distance of three meters)* .—Dark-red.

*Color (tip, margin & center.*—Red approximately R.H.S. 45B.

*Color (base).*—Dark pink red, approximately R.H.S. 45D.

*Form.*—Circular with a diameter of approximately 5 cm and approximately 15 petals per flower.

*Markings.*—Slightly darker veins at the base of the upper petals.

Bud:

*Shape.* —Elliptic.

*Color (immature).*—Green, no anthocyanin.

*Color (mature).*—Red.

Reproductive organs:

*Androecium.*—3–7 fertile anthers; white filaments; orange pollen.

*Gynoecium.*—5–6 lobed stigma; red style and stigma.

Spring flowering response period: Approximately 1.6 umbels opened 16 weeks after planting of unrooted cuttings (pinched plants) the plant does not stop flowering at seed set; the plant does not need pinching to induce further flower bud formation.

Outdoor flower production: 80—80 umbels per plant from April–May throughout September–October.

Durability: Shatter resistance is good.

Plant

General appearance:

*Height.*—50–60 cm. in August.

*Branching pattern.*—4–5 branches per plant.

*Internode length.*—20–30 mm.

Foliage:

*Color (margin).*—Medium-green, approximately R.H.S. 146A.

*Color (center).*—Medium-green.

*Form.*—Approximately 5 to 10 cm wide and 3 to 6.5 cm long.

*Margin.*—Approximately 9 indentations per leaf.

*Tolerance of botrytis.*—Good.

What is claimed is:

1. A new and distinct cultivar of geranium plant named 'Guisol' as illustrated and described.

* * * * *